(12) United States Patent
Johnson et al.

(10) Patent No.: US 6,258,976 B1
(45) Date of Patent: Jul. 10, 2001

(54) PROCESS FOR THE PREPARATION OF POLYAMINES AND POLYAMINE DERIVATIVES

(76) Inventors: Francis Johnson; Ramesh C. Gupta, both of c/o Chem-Master International, Inc. P.O. Box 563, East Setauket, NY (US) 11733

( * ) Notice: Subject to any disclaimer, the term of this patent is extended or adjusted under 35 U.S.C. 154(b) by 0 days.

(21) Appl. No.: 09/272,102

(22) Filed: Mar. 19, 1999

Related U.S. Application Data
(60) Provisional application No. 60/047,528, filed on May 23, 1997.

(51) Int. Cl.$^7$ .................................................. C07C 261/00
(52) U.S. Cl. ......................... 560/159; 560/158; 564/468; 564/509; 564/511; 564/512; 564/240; 564/241
(58) Field of Search .................................... 560/159, 158; 564/468, 509, 511, 512, 240, 241

(56) References Cited

U.S. PATENT DOCUMENTS 3,320,229 * 5/1967 Szabo .
5,344,846 * 9/1994 Jakus .

\* cited by examiner

*Primary Examiner*—Samuel Barts
(74) *Attorney, Agent, or Firm*—Arent Fox Kintner Plotkin & Kahn, PLLC

(57) ABSTRACT

Disclosed are processes for the preparation of compounds of the formula (I): H2N—(CH2)n—A—(CH2)m—NH2, or (II): H2N—(CH2)n—NH—C(=NR1)—NH—(CH2)m—NH2, wherein n and m are each independently an integer from 2 to 8; A is selected from the group consisting of —NR1—, —NR1—(CH2)r—NR1— and —NR1—(CH2)r—NR1—(CH2)z—NR1—, wherein r and z are an integer ranging from 2 to 8; and R1 is hydrogen or a protecting group having a carbonyl group.

8 Claims, No Drawings

PROCESS FOR THE PREPARATION OF POLYAMINES AND POLYAMINE DERIVATIVES

This application claims priority from U.S. provisional Application Ser. No. 60/047,528, filed May 23, 1997. The present invention relates to a new method for preparing polyamines and derivatives thereof. New compounds are also provided having antitumor activity.

BACKGROUND OF THE INVENTION

Polyamines are considered essential in cell proliferation. The naturally occurring polyamines in mammalian cells are putrescine, spermidine and spermine. A wide variety of related amines are found in other organisms and may play critical roles in their physiology. Nevertheless, it is also known that the association of cationic polyamines with negatively charged DNA induces significant structural changes in DNA. Spermidine and spermine can cause DNA to condense and aggregate and induce reversible B-to-Z transition in certain DNA sequences (Marton, L. J. et al., *Annu. Rev. Pharmacol. Toxicol.,* 1995, 35: 55–91). This led the researches to focus their attention on the potential use of polyamines as antitumor drugs (Basu, H. S. et al., *Biochem. J.,* 1990, 269: 329–334; Yanlong Li et al., *J. Med. Chem.,* 1996, 39: 339–341).

In spite of the scientific interest raised in the last years by these compounds, relatively few papers have been published describing their synthesis.

The preparation of the spermine and spermidine analogues has been mainly accomplished up to now by condensing a diamine with acrylonitrile and by reducing the nitrile group via catalytic hydrogenation (J. Med. Chem., 7, 710–16 (1964); U.S. Pat. No. 5,097,072; U.S. Pat. No. 4,967,008; J. Pharm. Sciences, 70(8), 956–9 (1981)). The main limitation of this method is that using acrylonitrile only 3-C terminal amine chains are obtained. Other drawbacks are due to the difficulty of purification of the final compounds, which is often performed by vacuum distillation. In particular, when dicyanoethylated compounds are desired, they undergo extensive decomposition on distillation and therefor cannot be obtained in a pure form using this method. The toxicity of acrylonitrile, increased by its high volatility, may be another problem, especially in view of a large scale synthesis.

A further method that has been reported for the preparation of polyamines is the reduction of amide intermediates which can be obtained by condensing ω-amino acids with diamines or of α,ω-diacids with two equivalents of diamine (J. Med. Chem., 31, 1183–1190 (1988)). However we have found that this method does not allow to prepare with good yields all the derivatives, since especially the lower alkylenyl homologues give by-products in large amount during the reduction step.

More recently the preparation of unsymmetrically substituted polyamine analogues was also reported (J. Med. Chem., 36, 2998–3004 (1993)). However the described process does need the preparation of rather complex synthons containing simultaneously three different nitrogen protecting groups. This results in a long multistep procedure which is unsuitable for industrial purposes. Moreover, the use of a mesityl protecting group is also unsuitable, since it requires acidic conditions for cleavage which can largely impair the flexibility of the method.

We have now found a new advantageous process for synthesizing polyamine derivatives.

SUMMARY OF THE INVENTION

The present invention provides a process for the preparation of polyamines of formula (I):

$$H_2N-(CH_2)_n-A-(CH_2)_m-NH_2 \qquad (I)$$

in which:
n and m, which an be the same or different, are an integer from 2 to 8;
A is $-NR^1-$, $-NR^1-(CH_2)_r-NR^1-$ or $-NR^1-(CH_2)_r-NR^1-(CH_2)_z-NR^1-$, wherein r and z are an integer ranging from 2 to 8 and $R^1$ is hydrogen or a carbonyl-containing protecting group, such as a tert-butoxycarbonyl group.

More particularly, there is provided a process for the synthesis of polyamines of formula (Ia), (Ib) and (Ic):

$$H_2N-(CH_2)_n-NR^1-(CH_2)_m-NH_2 \qquad (Ia)$$

$$H_2N-(CH_2)_n-NR^1-(CH_2)_r-NR^1-(CH_2)_m-NH_2 \qquad (Ib)$$

$$H_2N-(CH_2)_n-NR^1-(CH_2)_r-NR^1-(CH_2)_z-NR^1-(CH_2)_m-NH_2 \qquad (Ic).$$

The new process is accomplished by means of a simple multistep procedure which makes use of a 2-nitrobenzenesulfonyl protecting group as both a protecting and an activating group for the nitrogen atom to be functionalized. This protecting group has recently been described as a protecting group for benzylamines (Tetrahedron Letters, 36(36), 6373–4 (1995)) which requires a neutral cleavage and it provided particularly suitable for our process, especially in combination with a carbonyl-containing protecting group, such as a tert-butoxycarbonyl group.

The process of the present invention has some advantages with respect to the prior art methods, such as (i) a high flexibility, which allows the preparation of a broad series of polyamines both symmetrical and unsymmetrical with various length of the alkylene chains; (ii) high yields with no need for further purification of the products; (iii) possibility to obtain easily BOC-protected intermediates useful for further chemical processing.

Another object of the present invention is to provide a process for obtaining polyamine derivatives of formula (II):

$$H_2N-(CH_2)_n-NH-C(=NR^1)-NH-(CH_2)_m-NH_2 \qquad (II)$$

wherein n, m and $R^1$ have the above meanings.

A further object of the present invention are the polyamine derivatives of formula (II), or salts thereof with pharmaceutically acceptable acids, having antitumor properties.

The polyamine derivatives of formulas (I) and (II), especially when $R^1$ is a tert-butoxycarbonyl group or another suitable carbonyl-containing protecting group (see Greene (1981) *Protective Groups in Organic Synthesis* for exemplary protecting groups), are also particularly suitable intermediates for the preparation of bridged compounds in which the linker is a polyamine moiety, such as for example bis-platinum complexes. For ease of reference, only tert-butoxycarbonyl is exemplified in this application. However, a worker of skill in the art would be able to choose another suitable carbonyl-containing protecting group for use in accordance with the present invention. Other suitable carbonyl-containing protecting groups are thus contemplated within the scope of the present invention.

DETAILED DESCRIPTION OF THE INVENTION

The process for the preparation of the polyamines of formula (Ia) is accomplished according to the following steps:

(1) alkylation of 2-nitrobenzenesulfonamide with one equivalent of a phthaloylalkyl halide of formula (III):

$$Phth=N-(CH_2)_n-Hal \quad (III)$$

in which Phth=N— is a phthalimido group, n has the above meaning and Hal is a halogen atom, such as chlorine, bromine or iodine. This reaction is performed in the presence of a base, preferably an alkaline or alkaline-earth carbonate or bicarbonate, more preferably potassium carbonate. A solvent may be used, such as acetonitrile; the reaction temperature ranges from room temperature to the boiling point of the solvent;

(2) further alkylation of the intermediate product of step (1) with a halide of formula (IIIa):

$$Phth=N-(CH_2)_m-Hal \quad (IIIa)$$

in which Phth=N—, m and Hal are as above described. The reaction can be performed in the same conditions of step (1);

3) removal of the 2-nitrobenzenesulfonyl group by means of thiophenol/triethylamine in acetonitrile, as described in Tetrahedron letters, 36(36), 6373–4 (1995);

(4) protection of the central nitrogen atom by reaction with a protecting group containing a carbonyl group, such as di-tert-butyldicarbonate ((Boc)$_2$O) in the presence of a base, such as aqueous sodium bicarbonate;

(5) hydrolysis of the two phthalimido groups by reaction with hydrazine in a solvent, to give the compounds of formula (Ia) in which $R^1$ is tert-butoxycarbonyl group.

If the polyamines with $R^1$=hydrogen are desired, a simplified procedure can be employed, in which the intermediate from step (3) is simply hydrolyzed with hydrazine (reaction conditions of step (4)) to give the wanted polyamines.

The process for the preparation of the polyamines of formula (Ib) is accomplished according to the following steps:

(6) reaction of a diamine of formula H$_2$N—(CH$_2$)$_r$—NH$_2$ with two equivalents of 2-nitrobenzenesulfonyl chloride in a solvent such as methylene chloride and in the presence of a base such as triethylamine;

(7) sequential alkylation of the intermediate from step (6) with halides of formula (III) and (IIIa) in the same conditions described in the above step (1);

(8) removal of the two 2-nitrobenzenesulfonyl groups as described in the above step (3);

(9) protection of the two internal nitrogen atoms with carbonyl-containing protecting groups, such as tert-butoxycarbonyl groups, as described in the above step (4);

(10) hydrolysis of the two phthalimido groups as described in the above step (4), to give the compounds of the formula (Ib) in which $R^1$ is tert-butoxycarbonyl group.

Again, if the polyamines with $R^1$=hydrogen are desired, they can be obtained directly by hydrolysis of the two phthalimido groups in the intermediate product from step (8).

The process for the preparation of the polyamines of formula (Ic) is accomplished according to the following steps:

(11) hydrolysis, in the product from the above step (2) of formula:

$$Phth=N-(CH_2)_n-N(NPS)-(CH_2)_m-N=Phth$$

in which NPS is the 2-nitrobenzenesulfonyl group, of the two phthalimido groups as described in step (5) above;

(12) reaction of the product from step (11) with two equivalents of 2-nitrobenzenesulfonyl chloride as described in step (6) above to give an intermediate of formula $$NPS-NH-(CH_2)_n-N(NPS)-(CH_2)_m-NH-NPS$$

(13) sequential alkylation of the intermediate from step (12) with halides of formula (IV) and (IVa) as described in step (7) above:

$$Phth=N-(CH_2)_r-Hal \quad (IV)$$

$$Phth=N-(CH_2)_z-Hal \quad (IVa)$$

(14) removal of all the 2-nitrobenzenesulfonyl groups present in the intermediate from step (13) as described in step (3) above;

(15) reaction of the product from step (14) with three equivalents of a carbonyl-containing protecting group such as di-tert-butyldicarbonate to give an intermediate of formula $$Phth=N-(CH_2)_r-N(BOC)-(CH_2)_n-N(BOC)-(CH_2)_m-N(BOC)-(CH_2)_z-N=Phth$$

in which BOC is a tert-butoxyl group;

(16) hydrolysis of the two phthalimido groups in the intermediate from step (15) as described in the above step (5) to give the compounds of formula (Ic) in which $R^1$ is a carbonyl-containing protecting group, such as a BOC group.

Also in this case, when a compound with $R^1$=hydrogen is desired, it can be obtained directly by hydrolysis of the two phthalimido groups in the intermediate from step (14).

In all the above reactions, the 2-nitrobenzenesulfonyl groups can be suitably replaced by the corresponding 4-nitro analogue or by the 2,4-dinitro analogue.

The intermediates (III), (IIIa), (IV) and (IVa) can be replaced by corresponding nitrile derivatives of formula (III'), (IIIa'), (IV') and (IVa'):

$$NC-(CH_2)_{n-1}-Hal \quad (III')$$

$$NC-(CH_2)_{m-1}-Hal \quad (IIIa')$$

$$NC-(CH_2)_{r-1}-Hal \quad (IV')$$

$$NC-(CH_2)_{z-1}-Hal \quad (IVa')$$

The alkylation is then performed under almost the same conditions as for the phthalimido halides while the hydrolysis of the cyano groups is accomplished according to the methods described in the literature, in particular via catalytic hydrogenation in the presence of nickel Raney.

Another object of the present invention is to provide new polyamine derivatives of formula (II), or salts thereof with pharmaceutically acceptable acids, and a process for their preparation.

The compounds of formula (II) can be prepared according to the following multistep process:

(a) reaction of an intermediate of formula (V):

$$NC-(CH_2)_{n-1}-N=C=S \quad (V)$$

with ammonia in a solvent such as dioxane, followed by reaction with a carbonyl group-containing protecting group, such as di-tert-butyldicarbonate, in a solvent such as tetrahydrofuran to give a thiourea of formula (VI):

$$NC-(CH_2)_{n-1}-NHC(=S)NH-Prot \quad (VI).$$

The reaction with ammonia is performed at temperatures ranging from 0° C. to 50° C., preferably between 10° C. and room temperature. If di-tert-butyldicarbonate is used as the carbonyl group-containing protecting group (Prot), the reaction is preferably performed in the presence of a base such as an hydride, sodium hydride being the preferred one, and at low temperatures (between −15° C. and 0° C., preferably −10° C.);

(b) coupling of the protected-derivative of formula (VI) with an amine of formula (VII):

$$H_2N—(CH_2)_m—NHC—Bas \qquad (VII),$$

where Bas is a basic labile group, such as trifluoroacetyl, in the presence of a condensing agent such as a carbodiimide, preferably 1-(3-dimethylaminopropyl)-3-ethylcarbodiimide hydrochloride (WSC) and of a base such as triethylamine, followed by hydrolysis of the trifluoroacetyl group in basic conditions, preferably in aqueous methanol and in the presence of potassium carbonate, to give the guanidino derivative of formula (VIII):

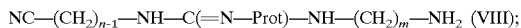

$$NC—(CH_2)_{n-1}—NH—C(=N—Prot)—NH—(CH_2)_m—NH_2 \quad (VIII);$$

(c) reduction of the nitrile group is intermediate (VIII), preferably by catalytic hydrogenation with nickel Raney as a catalyst, to give the compounds of formula (II) with $R^1$=Prot, which can further be converted into the analogues with $R^1$=hydrogen by removal of the Prot group in the usual conditions, such as with a mild acid at elevated temperatures or a strong acid at room temperature.

In the method described above, the trifluoroacetyl group can be replaced by a different basic labile group. Reference is again made to Greene (1981) *Protective Groups in Organic Synthesis* for suitable basic labile groups.

The intermediates of formula (V) may be prepared according to the method described in McKay et al., J. Am. Chem. Soc., 81, 4328 (1959), which is herein incorporated by reference, by reaction of a suitable ω-aminoalkylnitrile with carbon disulfide in the presence of triethylamine, followed by the addition of ethyl chloroformate.

The protected diamines of formula (VII) can be prepared as described in the following preparation 1.

The compounds of formula (II), especially when $R^1$ is hydrogen, can be used in the treatment of all those tumors susceptible to treatment with spermine, spermidine or other polyamines. For examples of such tumors, reference is made to U.S. Pat. No. 5,498,522.

The compounds of formula (II) may be used as active ingredients of therapeutic compositions to induce regression and/or palliation of cancers in mammals when administered in amounts ranging from about 1 mg to about 0.4 g per kilogram of body weight. A preferred dosage regimen would be from about 1 mg to about 50 mg per kilogram of body weight per day. Unit dosage may be employed so that from about 70 mg to about 3.5 g of the active compound for a subject of about 70 kg of body weight are administered in a 24-hour period. The dosage may be adjusted to be compatible to other treatment regimens, such as radiation therapy.

The pharmaceutical compositions may be in the form of tablets, capsules, gel capsules, suppositories, lyophilized powders and solutions for intravenous administration and can contain suitable excipients which can vary according with the type of the desired composition. Said compositions are prepared following procedures wellknown to the skilled in the art.

The invention is illustrated by the following examples.

Preparation 1—N-trifluoroacetamido-1,7-diaminoheptane

A solution of ethyl trifluoroacetate (10.65 g) dissolved in methanol (50 ml) was added slowly into a stirred solution of 1,7-diaminoheptane (19.5 g) in methanol (200 ml) containing triethylamine (20 ml) at 0 to −5° C. The reaction mixture was stirred overnight at room temperature and the solvent was evaporated on a rotary evaporator. The residue was distilled under vacuum at 0.25 mm Hg. The first distillate at 100 to 110° C. was identified as starting material and the second distillate at 120–130° C. was the required product isolated as an oil (8.5 g).

EXAMPLE 1

N,N'-bis(2-nitrosulfonyl)-1,4-diaminobutane

To a solution of putrescine (7.21 g) in dry methylene chloride (200 ml) was added triethylamine (18.2 g, dried over calcium hydride) and the solution was cooled in an ice-bath.

2-Nitrobenzenesulfonyl chloride (40 g) was added slowly to the reaction mixture so that the temperature of the reaction did not go above 25° C. The reaction mixture was stirred at room temperature overnight. It was cooled in an ice-bath and water (200 ml) was added. After stirring for a few minutes, methylene chloride was removed on the rotary evaporator and the desired sulfonamide precipitated from the reaction mixture. It was filtered, washed with water (300 ml) then with an aqueous saturated solution of sodium bicarbonate (200 ml) and finally again with water (300 ml). It was dried in air, then added to methanol (300 ml). The mixture was heated and stirred for 30 minutes (did not dissolved completely), cooled in an ice-bath and filtered. The solid cake was washed with methanol (50 ml) then dried under vacuum at 50° C. over $P_2O_5$ to give 32.5 g of the product, m.p. 184–185° C.

EXAMPLE 2

N,N'-bis(2-nitrosulfonyl)-N,N'-bis(4-cyanobutyl)-1,4-diaminobutane

To a solution of the bis-sulfonamide of example 1 (30.48 g) in acetonitrile (200 ml) was added potassium carbonate (27.6 g) followed by 5-bromovaleronitrile (21.36 g). The reaction mixture was then heated under reflux overnight. At this stage, additional bromovaleronitrile (1.5 g) was added and the reaction mixture was heated for a further 24 hours. The excess of potassium carbonate and potassium bromide by-product were removed by filtration and the filtrate was evaporated. The residue, a crystalline compound, was heated in methanol (200 ml) to remove impurities, cooled in an ice-bath and filtered. The solid cake was washed with cold methanol. The compound was dried under vacuum at 40–50° C. to give 37.2 g of the product, m.p. 115–117° C.; TLC $CH_2Cl_2$—MeOH (95:5), Rf 0.33.

EXAMPLE 3

N,N'-bis(4-cyanobutyl)-1,4-diaminobutane

To a solution of the product of example 2 (37.2 g) in acetonitrile (200 ml) was added thiophenol (15 ml) followed by potassium carbonate (52 g). After 10 minutes, the solution became quite thick. More acetonitrile (100 ml) was added and the reaction mixture was stirred at room temperature overnight. The reaction initially was slightly exothermic and was cooled in a water bath. The reaction was complete at this point as indicated by TLC ($CH_2Cl_2$—MeOH 95:5), Rf starting material 0.55; Rf product 0.15. The solvent was evaporated, water was added to the residue (100 ml) and the organic product was extracted with methylene chloride (3×75 ml). From the organic layer, the required diamine was extracted with 3M hydrochloric acid (about 100 ml) as dihydrochloride salt. The excess hydrochloric acid was removed on a rotary evaporator and ethanol was added to the residue. The product (14 g) crystallized out as the dihydrochloride in colorless crystals, m.p. 255–257° C.

EXAMPLE 4

N,N'-bis(4-cyanobutyl)-N,N'-bis(t-butyloxycarbonyl)-1,4-diaminobutane

To the dihydrochloride of example 3 (9.69 g) in water (50 ml) was added dry sodium bicarbonate (7.56 g) followed by di-tert-butyldicarbonate ((Boc)$_2$O; 14.38 g) and methylene chloride (50 ml). The mixture was stirred at room temperature overnight. The organic layer was separated, the aqueous layer was extracted with methylene chloride (2×20 ml) and the combined organic extracts were washed with 0.2M hydrochloric acid (20 ml) until the aqueous solution remained acidic. The organic layer was then washed with 5% aqueous sodium bicarbonate (5 ml), dried over magnesium sulfate and evaporated to give a liquid residue (14.4 g). This material was stirred with n-hexane (2×50 ml) and the n-hexane layer, after cooled in ice, was decanted. This removed residual (Boc)$_2$O. The product (11.2 g) was obtained as a syrup. Concentration of the n-hexane layer gave another 1 g of the product. Total yield 12.2 g, TLC CH$_2$Cl$_2$—MeOH (95:5), Rf 0.52.

(Boc)$_2$O was separated by its differential solubility in hexane vs. the product. Where the product has some minor solubility in hexane, this can be recovered by concentration of the hexane extract, when the product separates as an oil and is recovered by decantation of the hexane layer which contains the residual (Boc)$_2$O.

EXAMPLE 5

N,N'-bis(5-aminopentyl)-N,N'-bis(t-butyloxycarbonyl)-1,4-diaminobutane

A solution of the dinitrile derivative of example 4 (9 g) in anhydrous ethanol (150 ml) was saturated with NH$_3$ gas at 0° C. Raney Nickel catalyst (6 ml) washed with 3 to 4 times ethanol was added to the cold solution and the mixture was hydrogenated at about 50 psi overnight. The reaction was monitored by TLC and was only 50% complete at this state. The Raney Nickel catalyst was replaced and the hydrogenation continued overnight when the reaction was found to be complete. The catalyst was removed by filtration, the filtrate was treated with charcoal (S-51), filtered again and the solvent was removed on a rotary evaporator. The last traces of the solvent were removed on vacuum pump and the residue, which was a thick syrup with a greenish tinge, was identified as the required diamino derivative, 6.2 g.

EXAMPLE 6

N,N'-bis(2-nitrosulfonyl)-1,2-diaminoethane

A solution of 2-nitrobenzenesulfonyl chloride (40 g) in methylene chloride (150 ml) was added slowly to a stirred solution of methylene chloride (150 ml) containing ethylene diamine (4.9 g) and triethylamine (18.2 g) at 0° C. The reaction was continued at room temperature for 24 hours and filtered to remove the triethylamine hydrochloride. On addition of water (200 ml) to the organic solution a white precipitate was obtained. After the separation of the layers, the material that was insoluble in methylene chloride was obtained by filtration. It was then recrystallized from methanol to give the product (30 g) as colorless crystals, m.p. 115° C. (dec.); TLC solvent system DCM, Rf 0.2.

EXAMPLE 7

N,N'-bis(2-nitrosulfonyl)-N,N'-bis(6-phthalimidohexyl)-1,2-diaminoethane

A mixture of N,N'-bis(2-nitrosulfonyl)-1,2-diaminoethane (5 g; example 6), potassium carbonate (4.8 g) and N-(6-bromohexyl)phthalimide (7.93 g) in 35 ml of dimethylformamide were stirred and heated to 80° C. for 4 hours. After allowing the reaction mixture to come to room temperature, the contents were poured into water (100 ml) and the solid that was obtained was filtered, washed with methanol and dried in a oven for P$_2$O$_5$ at 50° C. to give 9.27 g of the product as a pale yellow solid, m.p. 148–149° C.

EXAMPLE 8

N,N'-bis(6-phthalimidohexyl)-1,2-diaminoethane, Dihydrochloride Salt

To a stirred suspension of the product of Example 7 (21.99 g) and potassium carbonate (20.44 g) in acetonitrile (220 ml), a solution of thiophenol (6.6 g) in acetonitrile (20 ml) was added at room temperature and the stirring was continued for 24 hours. The reaction mixture was filtered to remove inorganic solids and the organic layer was concentrated at reduced pressure. The residue was taken into methylene chloride (100 ml) and washed with 2N hydrochloric acid (2×20 ml). The hydrochloride of the product, obtained as a fine suspension, was filtered using glass filter paper and the precipitate was washed with diethyl ether to give 5.7 g of the product as crystals, m.p. 232° C.

EXAMPLE 9

N,N'-bis(t-butyloxycarbonyl)-N,N'-bis(6-phthalimidohexyl)-1,2-diaminoethane

To a stirred suspension of the dihydrochloride of example 8 (5.6 g) in methylene chloride (30 ml) at 0° C., sodium bicarbonate (1.6 g) dissolved in water (5 ml) was added. After the complete neutralization of the hydrochloride, di-tert-butyldicarbonate (6.2 g) was added and the stirring was continued for 12 hours at room temperature. The CH$_2$Cl$_2$ layer was separated, dried over sodium sulfate, filtered and concentrated to furnish the desired product as a viscous oil (6.12 g); TLC solvent system CH$_2$Cl$_2$—MeOH (9:1), Rf 0.7. On standing in hexane, it gave colorless crystals, m.p. 96° C.

EXAMPLE 10

N,N'-bis(6-aminohexyl)-N,N'-bis(t-butyloxycarbonyl)-1,2-diaminoethane

A solution of anhydrous hydrazine (1 ml) was added to a stirred mixture of anhydrous ethanol (30 ml) and methylene chloride (20 ml) containing N,N'-bis(t-butyloxycarbonyl)-N,N'-bis(6-phthalimidohexyl)-1,2-diaminoethane (2.8 g; example 9). The reaction was continued overnight and the precipitated phthalazinedione by-product was removed by filtration. The filtrate on concentration at reduced pressure gave the title compound (1.5 g) as an oil.

EXAMPLE 11

N-(5-cyanopentyl)thiourea

To a 0.5M solution of ammonia in dioxane (80 ml) at 10° C. was added 5-cyanopentyl isothiocyanate (5 g) and the solution was stirred at room temperature overnight. TLC of the reaction mixture still showed the presence of some starting material. Additional ammonia in dioxane (40 ml) was added and the solution was stirred for a further 6 hours. At this stage, the reaction was found to be complete as judged by TLC analysis. The solvent was then removed on a rotary evaporator and to the residue was added methyl tert-butyl ether (40 ml). The mixture was then heated on steam bath briefly (the solid did not dissolve) then cooled to give the required product as a colorless crystalline material (5 g), m.p. 69–71° C.

EXAMPLE 12

N-(5-cyanopentyl)-N'-(t-butyloxycarbonyl)thiourea

To a solution of the thiourea of example 11 (1.026 g) in tetrahydrofuran (60 ml) at −10° C. to 0° C. under nitrogen was added sodium hydride (520 mg) and the reaction mixture was stirred at the same temperature for 40 minutes. Di-tert-butyldicarbonate (1.526 g) was added and the mixture was stirred, the temperature being allowed to rise to room temperature overnight. Brine (20 ml) was added to the reaction mixture and most of the tetrahydrofuran was removed on a rotatory evaporator at about 40° C. to the residue was added ethyl acetate (30 ml) and the resulting solution was washed with brine (10 ml), dried over magnesium sulfate and evaporated. The residue was treated with n-hexane (2×20 ml), cooled in ice and decanted to remove excess (Boc)$_2$O if present. The syrupy residue was then crystallized twice from methyl tert-butyl ether-hexane to give colorless crystals of the product (0.82 g), m.p. 83–85° C. A further 10 to 15% of the material was obtained by chromatography on a silica gel using CH$_2$Cl$_2$ as the eluant.

EXAMPLE 13

N-(7-trifluoroacetamidoheptyl)-N'-(t-butyloxycarbonyl)-N''-(5-cyanopentyl)guanidine To a solution of the thiourea derivative of example 12 (8 g) in dimethylformamide (10 ml) was added the trifluoroacetamido derivative of preparation 1 (7.5 g). Triethylamine (12ml) and 1-(3-dimethylaminopropyl)-3-ethylcarbodiimide hydrochloride (8.5 g) were then added and the solution was stirred at room temperature for about 6 hours (at this point, TLC showed no starting thiourea to be present). To the mixture was then added ethyl acetate (100 ml) and the solution was washed with water (2×20 ml). The organic layer (pH about 10) was treated with ice-cold aqueous 2N hydrochloric acid until the aqueous layer attained a pH of 4.8 units. This removes unwanted basic material while leaving the desired product in the organic phase. Below pH 4.8 the product also is extracted into the aqueous phase. After removing the unwanted basic material, the solution was washed with brine, dried and evaporated to give a residue (13.8 g) which, by TLC analysis, was a mixture of 4 compounds. These were separated by silica gel column chromatography using ethyl acetate-hexane (6:4), then pure ethyl acetate as the eluants. The latter fraction (7 g) contained the required product as a syrup.

EXAMPLE 14

N-(7-aminoheptyl)-N'-(t-butyloxycarbonyl)-N''-(5-cyanopentyl)guanidine

To a solution of the product of example 13 (6.9 g) in methanol (50 ml) was added aqueous potassium carbonate (2.76 g dissolved in 20 ml of water) and the mixture was stirred at room temperature overnight. The solvent was removed at less than 40° C. on a rotary evaporator and the residual liquid was extracted three times with methylene chloride-isopropanol mixture (9:1; 60 ml; 30 ml; 25 ml). This extract was washed with brine, dried over sodium sulfate and evaporate to give 5.4 g of the product as a viscous oil.

EXAMPLE 15

N-(7-aminoheptyl)-N'-(6-aminohexyl)-N''-(t-butyloxycarbonyl) guanidine

The guanidino derivative of example 14 (5.4 g) was dissolved in dry ethanol (80 ml) and the solution was saturated with ammonia gas at 0° C. Raney nickel catalyst (about 5 ml) washed 3 to 4 times with ethanol was added and the mixture was hydrogenated at 50–55 psi overnight, at which point the reaction was only 40% complete. The catalyst was replaced twice more to bring the reduction to completion. Evaporation of the solvent on a rotary evaporator then gave the desired product in quantitative yield as a syrup.

What is claimed is:

1. A process for producing a compound of formula (II)

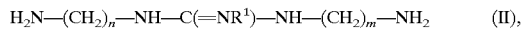

wherein n and m are each independently an integer from 2 to 8; and R$^1$ is a protecting group having a carbonyl group, the process comprising:

(a) reacting a compound of formula (V)

wherein n is as described above, with ammonia;

(b) protecting the compound of formula (V) with a protecting group having a carbonyl group, to produce a compound of formula (VI)

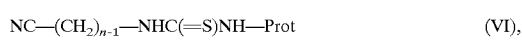

wherein n is as described above and Prot is the protecting group;

(c) coupling the compound of formula (VI) with a compound of formula (VII)

wherein m is as described above and Bas is a basic labile group;

(d) hydrolyzing the basic labile group, to produce a compound of formula (VIII)

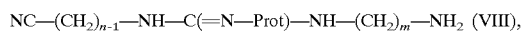

wherein n, m and Prot are as described above; and (e) reducing the nitrile group in the compound of formula (VIII), to produce a compound of formula (II).

2. The process of claim 1, further comprising, after step (e), cleaving the protecting group with an acid to produce a compound of formula (II) wherein R$^1$ is hydrogen.

3. A process for producing a compound of formula (Ia)

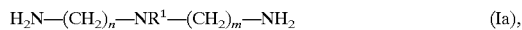

wherein n and m are each independently an integer from 2 to 8; and R$^1$ is a protecting group having a carbonyl group, the process comprising:

(a) alkylating a nitrobenzenesulfonamide selected from the group consisting of 2-nitrobenzenesulfonamide, 4-nitrobenzenesulfonamide and 2,4-dinitrobenzenesulfonamide with one equivalent of a compound of formula (III) or (III')

wherein Phth=N— is a phthalimido group is as described above and Hal is a halogen atom;

(b) alkylating the product of step (a) with a compound of formula (IIIa) or (IIIa')

wherein Phth=N—, m and Hal are as described above;

(c) removing the nitrobenzenesulfonyl group from the product of step (b);

(d) protecting the central nitrogen atom of the product of step (c) with a protecting group having a carbonyl group; and (e) hydrolyzing the two phthalimido groups by reacting the product of step (d) with hydrazine, or (f) reducing the two cyano groups of the product of step (d) by catalytic hydrogenation to produce a compound of formula (Ia).

4. A process for producing a compound of formula (Ia)

$$H_2N—(CH_2)_n—NR^1—(CH_2)_m—NH_2 \quad (Ia),$$

wherein n and m are each independently an integer from 2 to 8; and $R^1$ is hydrogen, the process comprising:

(a) alkylating a nitrobenzenesulfonamide selected from the group consisting of 2-nitrobenzenesulfonamide, 4-nitrobenzenesulfonamide and 2,4-dinitrobenzenesulfonamide with one equivalent of a compound of formula (III) or (III')

wherein Phth=N— is a phthalimido group, n is as described above and Hal is a halogen atom;

(b) alkylating the product of step (a) with a compound of formula (IIIa) or (IIIa')

wherein Phth=N—, m and Hal are as described above;

(c) removing the nitrobenzenesulfonyl group from the product of step (b);

(d) hydrolyzing the two phthalimido groups by reacting the product of step (c) with hydrazine, or (e) reducing the two cyano groups of the product of step (c) by catalytic hydrogenation to produce a compound of formula (Ia).

5. A process for producing a compound of formula (Ib)

$$H_2N—(CH_2)_n—NR^1—(CH_2)_r—NR^1—(CH_2)_m—NH_2 \quad (Ib),$$

wherein n, m and r are each independently an integer from 2 to 8; and $R^1$ is a protecting group having a carbonyl group, the process comprising:

(a) reacting a compound of formula $H_2N—(CH_2)_r—NH_2$, wherein r is as described above, with two equivalents of a nitrobenzenesulfonyl chloride selected from the group consisting of 2-nitrobenzenesulfonyl chloride, 4-nitrobenzenesulfonyl chloride and 2,4-dinitrobenzenesulfonyl chloride;

(b) alkylating the product of step (a) with one equivalent of a compound of formula (III) or (III')

wherein Phth=N— is a phthalimido group, n is as described above and Hal is a halogen atom;

(c) alkylating the product of step (b) with a compound of formula (IIIa) or (IIIa')

wherein Phth=N—, m and Hal are as described above;

(d) removing the two nitrobenzenesulfonyl groups from the product of step (c);

(e) protecting the two internal nitrogen atoms with protecting groups each having a carbonyl group; and (f) hydrolyzing the two phthalimido groups by reacting the product of step (e) with hydrazine, or (g) reducing the two cyano groups of the product of step (e) by catalytic hydrogenation to produce a compound of formula (Ib).

6. A process for producing a compound of formula (Ib)

$$H_2N—(CH_2)_n—NR^1—(CH_2)_r—NR^1—(CH_2)_m—NH_2 \quad (Ib),$$

wherein n, m and r are each independently an integer from 2 to 8; and $R^1$ is hydrogen, the process comprising:

(a) reacting a compound of formula $H_2N—(CH_2)_r—NH_2$, wherein r is as described above, with two equivalents of a nitrobenzenesulfonyl chloride selected from the group consisting of 2-nitrobenzenesulfonyl chloride, 4-nitrobenzenesulfonyl chloride and 2,4-dinitrobenzenesulfonyl chloride;

(b) alkylating the product of step (a) with one equivalent of a compound of formula (IIIa) or (IIIa')

wherein Phth=N— is a phthalimido group, n is as described above and Hal is a halogen atom;

(c) alkylating the product of step (b) with a compound of formula (IIIa) or (IIIa')

wherein Phth=N—, m and Hal are as described above;

(d) removing the two nitrobenzenesulfonyl groups from the product of step (c); and (e) hydrolyzing the two phthalimido groups by reacting the product of step (d) with hydrazine, or (f) reducing the two cyano groups of the product of step (d) by catalytic hydrogenation to produce a compound of formula (Ib).

7. A process for producing a compound of formula (Ic)

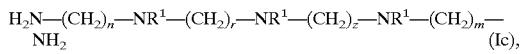

wherein n, m, r and z are each independently an integer from 2 to 8; and $R^1$ is a protecting group having a carbonyl group, the process comprising:

(a) alkylating a nitrobenzenesulfonamide selected from the group consisting of 2-nitrobenzenesulfonamide, 4-nitrobenzenesulfonamide and 2,4-dinitrobenzenesulfonamide with one equivalent of a compound of formula (III) or (III')

wherein Phth=N— is a phthalimido group, n is as described above and Hal is a halogen atom;

(b) alkylating the product of step (a) with a compound of formula (IIIa) or (IIIa')

wherein Phth=N—, m and Hal are as described above;

(c) hydrolyzing the two phthalimido groups by reacting the product of step (b) with hydrazine or reducing the two cyano groups of the product of step (b) by catalytic hydrogenation;

(d) reacting the product from step (c) with two equivalents of a nitrobenzenesulfonyl chloride selected from the group consisting of 2-nitrobenzenesulfonyl chloride, 4-nitrobenzenesulfonyl chloride and 2,4-dinitrobenzenesulfonyl chloride;

(e) alkylating the product of step (d) with one equivalent of a compound of formula (IV) or (IV')

wherein Phth=N—, r and Hal are as described above;

(f) alkylating the product of step (e) with a compound of formula (IVa) or (IVa')

wherein Phth=N—, z and Hal are as described above;

(g) removing all of the nitrobenzenesulfonyl groups present in the product of step (f);

(h) protecting the three internal nitrogen atoms with protecting groups each having a carbonyl group; and (i) hydrolyzing the two phthalimido groups by reacting the product of step (h) with hydrazine, or (j) reducing the two cyano groups of the product of step (h) by catalytic hydrogenation to produce a compound of formula (Ic).

8. A process for producing a compound of formula (Ic)

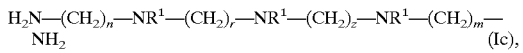

wherein n, m, r and z are each independently an integer from 2 to 8; and $R^1$ is hydrogen, the process comprising:

(a) alkylating a nitrobenzenesulfonamide selected from the group consisting of 2-nitrobenzenesulfonamide, 4-nitrobenzenesulfonamide and 2,4-dinitrobenzenesulfonamide with one equivalent of a compound of formula (III) or (III')

wherein Phth=N— is a phthalimido group, n is as described above and Hal is a halogen atom;

(b) alkylating the product of step (a) with a compound of formula (IIIa) or (IIIa')

wherein Phth=N—, m and Hal are as described above;

(c) hydrolyzing the two phthalimido groups by reacting the product of step (b) with hydrazine or reducing the two cyano groups of the product of step (b) by catalytic hydrogenation;

(d) reacting the product from step (c) with two equivalents of a nitrobenzenesulfonyl chloride selected from the group consisting of 2-nitrobenzenesulfonyl chloride, 4-nitrobenzenesulfonyl chloride and 2,4-dinitrobenzenesulfonyl chloride;

(e) alkylating the product of step (d) with one equivalent of a compound of formula (IV) or (IV')

wherein Phth=N—, r and Hal are as described above;

(f) alkylating the product of step (e) with a compound of formula (IVa) or (IVa')

wherein Phth=N—, z and Hal are as described above;

(g) removing all of the nitrobenzenesulfonyl groups present in the product of step (f); and (h) hydrolyzing the two phthalimido groups by reacting the product of step (g) with hydrazine, or (i) reducing the two cyano groups of the product of step (d) by catalytic hydrogenation to produce a compound of formula (Ic).

* * * * *